United States Patent [19]

Wendell et al.

[11] Patent Number: 4,947,686
[45] Date of Patent: Aug. 14, 1990

[54] METHOD AND APPARATUS FOR DETERMINING WEB TENSION SETTING

[75] Inventors: Richard H. Wendell, Golden; Tracy J. Fowler, Denver, both of Colo.

[73] Assignee: Adolph Coors Company, Golden, Colo.

[21] Appl. No.: 319,656

[22] Filed: Mar. 6, 1989

[51] Int. Cl.$^5$ ............................................. G01L 5/04
[52] U.S. Cl. ............................................................. 73/159
[58] Field of Search ................ 73/159, 789, 791, 794, 73/795, 800, 826, 866; 162/263, 198; 156/64

[56] References Cited

U.S. PATENT DOCUMENTS

| | | | |
|---|---|---|---|
| 1,505,127 | 8/1924 | Ayres | 73/159 |
| 2,568,731 | 9/1951 | Hansen et al. | 73/159 |
| 4,779,411 | 10/1988 | Kendall | 112/417 |

*Primary Examiner*—Robert Raevis
*Attorney, Agent, or Firm*—Klaas & Law

[57] ABSTRACT

An apparatus for use in determining the approximate web tension setting necessary for providing a predetermined web width in a machine, such as a web printer, which is used to process a continuous plastic web of the type which is subject to significant stretching and shrinking in response to relatively small web tension variations, comprising a first web restraining device for holdingly engaging a first end of a length of web material to be tested; a second web restraining device for holdingly engaging a second end of the length of web material to be tested; a force application device for applying a controlled amount of longitudinal stretching force to the length of web material to be tested; and a measuring device for measuring the width of the length of web material to be tested in a mid-region thereof during application of the longitudinal stretching force thereto. The apparatus may also be used for determining web graphics distortion.

3 Claims, 2 Drawing Sheets

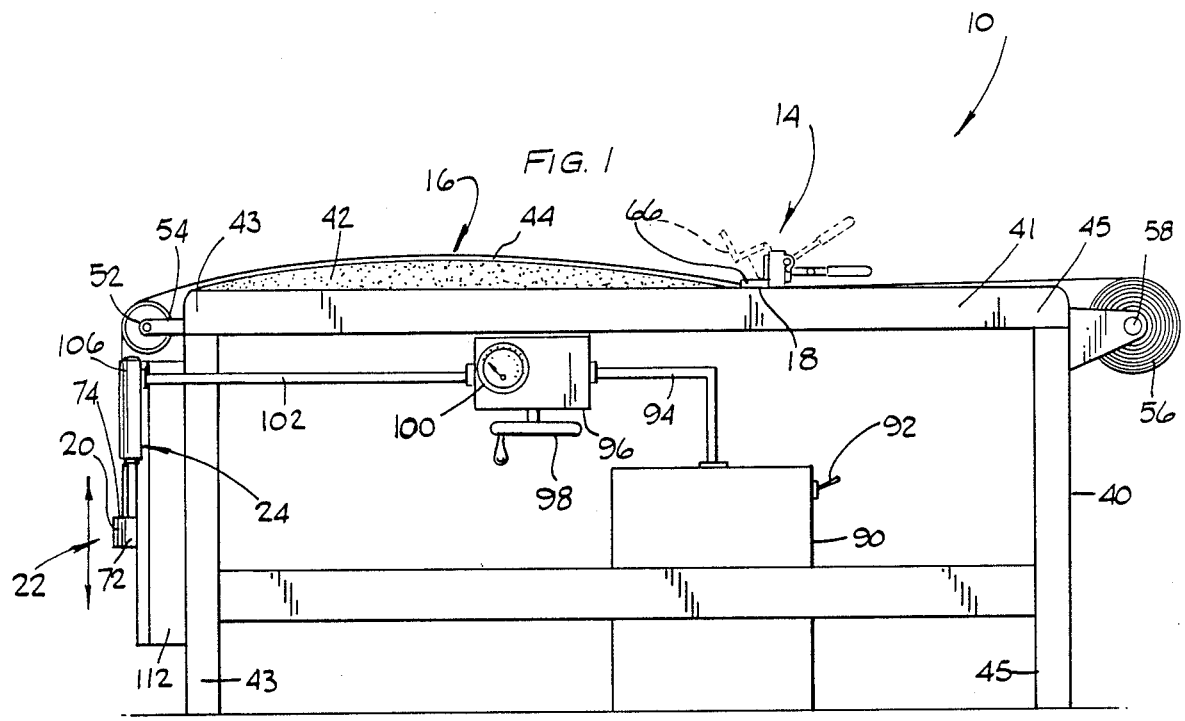
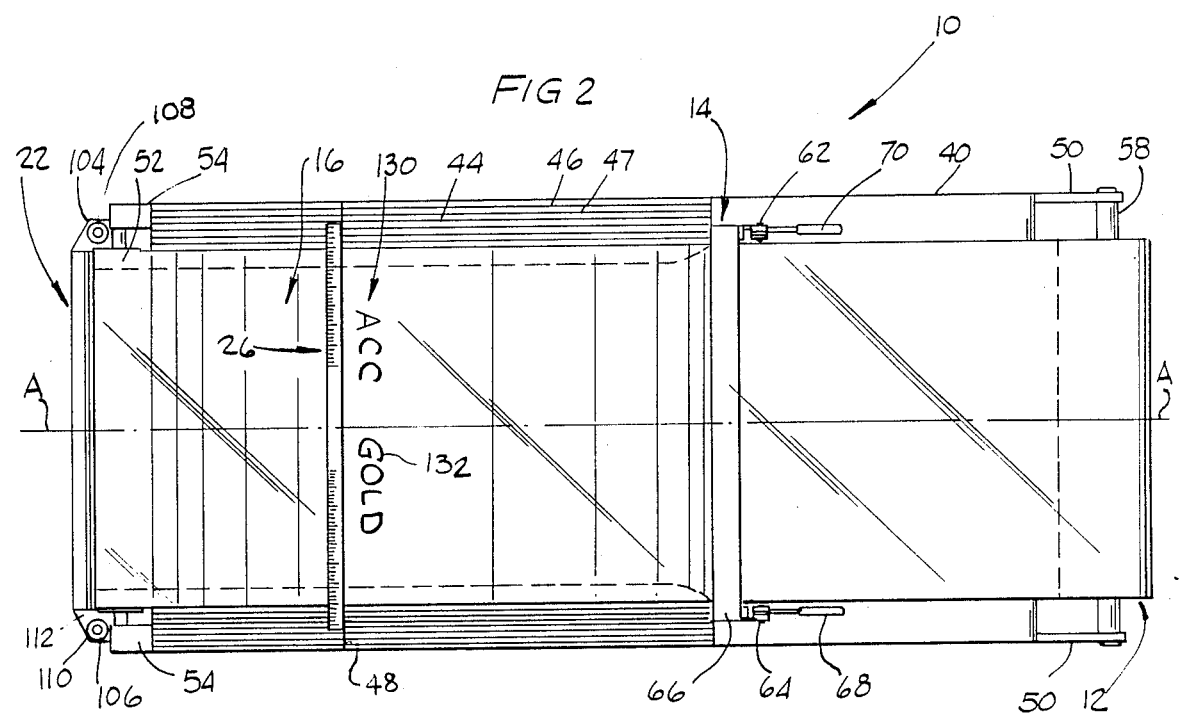

METHOD AND APPARATUS FOR DETERMINING WEB TENSION SETTING

BACKGROUND OF THE INVENTION

The present invention relates generally to web processing apparatus and, more particularly, to an apparatus for determining the approximate web tension setting necessary for providing a predetermined web width in a web processing machine, such as a web printer, which is used to process a continuous plastic web of the type which is subject to significant stretching and shrinking in response to relatively small web tension variations.

Composite webs such as described in U.S. Pat. No. 4,254,173 for COMPOSITE MATERIAL FOR SECONDARY CONTAINER PACKAGING of A. Dean Peer, Jr. (which is hereby specifically incorporated by references for all that it discloses), consist of a web of paper material adhered to a web of plastic film material. In the composite web forming process described in the Peer patent, the film web, prior to being laminated to the paper web, is printed with repeating graphics material which provide the visual display for packaging cartons or the like which are formed from the web in subsequent processing steps. In the manufacture of composite webs of the type described in Peer, a considerable cost savings may be achieved by use of "non-oriented" plastic films as opposed to "oriented" plastic films. However, non-oriented plastic films are considerably less stable than oriented films, i.e. non-oriented plastic films are much more susceptible to stretching both in a length and width direction in response to minor tension variations, temperature changes, etc., than oriented plastic films.

Methods and apparatus for measuring and controlling the dimensions of a web of plastic film prior to its lamination to a web of paper are disclosed in U.S. Pat. No. 4,496,417 of Haake et al.; U.S. Pat. No. 4,572,752 of Jensen et al.; U.S. Pat. No. 4,610,739 of Jensen, and U.S. Pat. No. 4,786,353 of Templeton et al., which are each hereby specifically incorporated by reference for all that is disclosed therein. The above referenced patents describe laminating devices which measure the relative elongation and/or the width of a repeat length portion of a moving web of relatively stretchable plastic film material The measurements thus made are used by an associated control system to vary an operating parameter of the system to maintain the web repeat length or width near a predetermined design value. However, it has been found that such control systems are most effective if the initial web tension setting of the associated web processing apparatus is approximately correct for the particular plastic web which is being processed. If the system tension setting is significantly different than the "ideal" tension setting for the particular web being processed, then the control system may experience trouble with accurately controlling the subject web parameter, i.e. web width or repeat length.

A similar problem exists in the printing of plastic film web which is to be laminated to a paper web by a lamination process such as described in U.S. Pat. No. 4,496,417 of Haake et al. Plastic film webs, when subjected to high tension forces in the longitudinal direction, tend to stretch in a longitudinal or lengthwise direction and, at the same time, tend to "neck down," i.e. decrease in width. It is desirable to print webs at a tension setting which provides a web width approximately equal to the desired web width of the finished laminated product. However, in the printing of non-oriented plastic film webs, the printing machine tension setting which is needed to provide a desired web width varies from roll to roll of web material. If the initial tension setting is approximately correct, then the control system provided on the printing machine can thereafter monitor web width and make small adjustments to web tension to provide the desired width. However, if the initial web tension setting is substantially different from the tension setting required to produce a desired width, then such printer control systems are often incapable of accurately providing the tension correction which is required.

Due to the fact that the behavior of non-oriented plastic films varies significantly from roll to roll, even when films of the same specification are purchased from the same manufacturer, it is quite important to accurately set the initial processing machine operating tension for each new roll of plastic film which is to be processed. Prior to the present invention, the method for determining an appropriate web tension setting for a particular roll of plastic film was to submit a sample of the film to a standardized elastic modules test such as described in attached Appendix A, which is hereby specifically incorporated by reference herein and which forms a part of the disclosure of this specification as though fully set forth herein. A problem with the use of such a test is that it is relatively expensive to perform, e.g. a typical lab charge for performing this test on a single roll of plastic film during 1988 is $150.00. Another problem is that such a test necessitates access to a laboratory with sophisticated testing equipment and highly skilled technicians. Another problem is that, even when such a laboratory is nearby, the testing often takes a considerable period of time to perform, e.g. ten days between the submission of samples and the return of the test results. Thus, a web processor is required to maintain a considerable inventory of plastic web rolls due to the lag time between the submission of test samples and the return of results.

Thus, a need exists for a method of quickly, accurately, and inexpensively testing a roll of plastic film material for determining a proper initial tension setting for a web processing machine such as a laminator or printer.

OBJECTS OF THE INVENTION

It is an object of the present invention to provide a method and apparatus for determining an approximate web processing machine tension setting for a web of relatively stretchable material such as non-oriented plastic film.

It is a further object of the present invention to provide a method and apparatus for quickly determining a web processing machine tension setting.

It is another object of the invention to provide a method and apparatus for measuring web print distortion at various tension settings.

It is another object of the present invention to provide an apparatus for determining a web processing machine tension setting which is relatively inexpensive to construct and which is relatively inexpensive to operate.

It is another object of the present invention to provide a method for determining a web processing machine tension setting which may be used by most machine operators without extensive technical training.

It is another object of the present invention to provide an apparatus for determining a web processing machine tension setting which may be installed in a relatively compact space near a web processing machine.

SUMMARY OF THE INVENTION

The present invention is directed to an apparatus for use in determining the approximate web tension setting necessary for providing a predetermined web width in a machine, such as a web printer, which is used to process a continuous plastic web of the type which is subject to significant stretching and shrinking in response to relatively small web tension variations. Such an apparatus may comprise a first web restraining assembly for holdingly engaging a first end of a length of web material to be tested; a second web restraining assembly for holdingly engaging a second end of the length of web material to be tested; a force application assembly for applying a controlled amount of longitudinal stretching force to the length of web material to be tested; and a measuring device for measuring the width of the length of web material to be tested in a mid-region thereof during application of the longitudinal stretching force thereto.

The present invention is also directed to a method for determining the approximate web tension setting for a continuous web processing machine of the type having a web unwind roll, a web draw roll and a processing station positioned between the unwind roll and draw roll which performs repetitive operations on the web wherein a web to be processed is a plastic web of the type which is subject to substantial stretching and shrinking in response to relatively small tension variations in the web and wherein the processing machine is of the type which requires a preset constant web width for proper web processing. The method may comprise: (a) providing a length of web material from a web roll that is to be processed; (b) restraining the length of web material against longitudinal movement at one end thereof; (c) engaging a second end of the web with a longitudinally movable clamping device; (d) applying a selected constant test force to the movable clamping device in a longitudinal direction so as to place the web under a constant, uniform tension; (e) measuring the width of the web after application of the test force thereto in a predetermined longitudinal region of the web; (f) recording the test force value and the measured web width associated therewith; (g) repeating steps (d), (e), and (f) for a plurality of different magnitude test forces; (h) based upon the plurality of recorded test force values and associated web widths, determining a force value corresponding to the preset constant web width for which the operating machine is designed; and (i) initially setting the web tension of the operating machine to a value corresponding to the determined force value.

BRIEF DESCRIPTION OF THE DRAWINGS

FIG. 1 is a side elevation view of a web testing apparatus.

FIG. 2 is a top plan view of the web testing apparatus of FIG. 1.

DETAILED DESCRIPTION OF THE INVENTION

Figure 3:
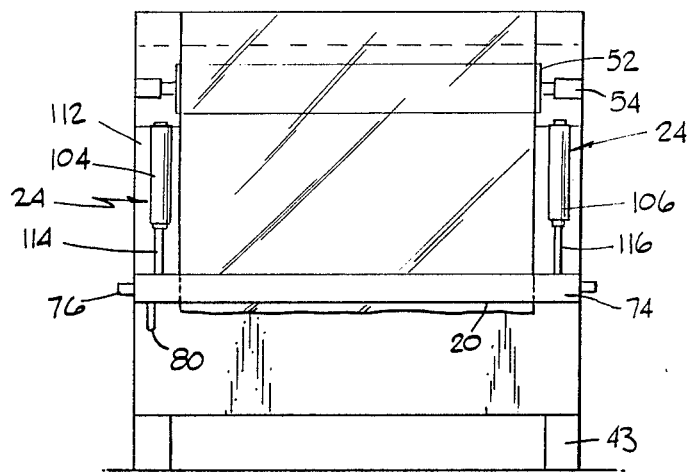
FIG. 3 is a front elevation view of the web testing apparatus of FIGS. 1 and 2.

FIGS. 1-3 illustrate an apparatus 10 for use in determining the approximate web tension setting necessary for providing a predetermined web width in a machine, such as a web printer, which is used to process a continuous plastic web of the type which is subject to significant stretching and shrinking in response to relatively small web tension variations. In general, the apparatus comprises a first web restraining means 14 for engaging a first end 18 of a length 16 of web material to be tested; a second web restraining means 22 for engaging and holding a second end 20 of the length of web material to be tested; force application means 24 for applying a controlled amount of longitudinal stretching force to the web material to be tested; and a measuring means 26 for measuring the width of the web material to be tested, in a mid-region thereof, during application of the longitudinal stretching force thereto. The measuring means 26 may also be used to measure web print distortion before and after application of stretching force to the web.

Having thus described the invention in general, specific features of the invention will now be described in further detail.

The apparatus 10 may comprise a table 40 having a horizontal table top 41 with a front end 43 and a rear end 45. As best illustrated by FIGS. 1 and 2, a convex member 42 having a central longitudinal axis AA may be mounted on the table top 41 at a forward end thereof. The convex member 42 has a relatively low-friction convex upper surface 44 which is elevated at a central portion thereof and which arcuately tapers down to the same elevation a the table top at front and rear end portions thereof. The convex member is of uniform longitudinal cross section from side to side.

A plurality of parallel, closely spaced, evenly spaced, longitudinally extending reference lines 46, 47, etc., may be provided on the upper surface of the convex member 42. A transversely extending reference line 4 which is positioned approximately at the mid-length of the film web material to be tested 16 is also provided on the convex upper surface 44 extending perpendicular to the longitudinal reference lines 46, 47, etc. In one preferred embodiment, the height of the convex member at its central portion may be approximately 2 inches, and the longitudinally extending cord length of the convex member 42, as measured along the table top 41, may be approximately 50 inches.

An idler roll 52 having a transverse dimension approximately equal to that of the table top may be mounted on an upper front end portion of the table 40 at an elevation where the surface of the roll 52 is approximately tangentially aligned with a tangent line extended from the forward edge of the convex surface 44. A film unwind roll 56 is rotatably mounted as by a bracket assembly 58 to an upper rear end portion of the table 40.

The first web restraining means 14 may comprise a transversely extending clamping assembly including spaced, vertical post members 62, 64, a transversely extending plate member 66 which is pivotally attached to the post member 62, 64. Locking handle members 68, 70 may be provided which are attached to end portions of the transverse plate member 66 enabling the transverse plate member to be pivoted from a raised positioned illustrated in phantom in FIG. 1 to a locked, lowered position illustrated in solid lines in FIG. 1 in which the transverse member 66 is positioned in firm abutting engagement with the table top 41. The transversely extending clamping assembly is adapted to engage the length of web material 16 across the entire width thereof to fixedly hold the engaged portion of the we in immobile relationship with the table top.

The second web restraining means 22 may comprise a second transversely extending clamping assembly including a first transversely extending member 72 having opposite ends thereof fixedly mounted on power cylinder pistons, as described in further detail below. The second transversely extending clamping assembly further comprises a second transversely extending member 74 which is pivotally mounted on the first transversely extending member as by a spring biased, pivotal mounting assembly 76 which is biased to hold the second member 74 in tight abutting contact with the first member 72 and which is pivotally displaceable therefrom by the use of a handle assembly 80 which is fixedly attached to the second transversely extending member 74. Both the first and second clamping assemblies may be of conventional commercially available types well known in the art.

The force application means 24 may comprise a conventional air compressor 90 which is operated through a conventional on/off switch 92. An air line 94 places the air compressor 90 in fluid communication with a control valve assembly 96 which may be actuated by control wheel 98 to provide a controlled amount of air pressure, indicated by a pressure gauge 100, to a downstream air line 102. The air line 102 communicates with conventional compressed air cylinder units 104, 106 which are actuated by the pressurized air in line 102. The air cylinder units have first ends 108 110 which are fixedly attached to a bracket assembly 112 which is in turn fixedly mounted on the forward end of table 40. Each of the compressed air cylinder units 104, 106 comprises an air-actuated piston 114, 116 which is urged downwardly by a force which is proportionate to the amount of air pressure provided in air line 102. Thus, application of pressurized air to air line 102 provides a longitudinally directed stretching force to the length of film material 16 engaged by the first and second web restraining means 14, 22, the second clamping assembly being longitudinally displaceable relative the first clamping assembly by the compressed air cylinder units 104, 106.

The measuring means 26 may comprise a conventional straightedge ruler which is preferably graduated in units of 1/100 of an inch. The ruler may be positioned in alignment with transverse reference line 48 for measuring the width of the web 16 at a mid-portion thereof subsequent to application of a predetermined amount of force thereto.

Operation of apparatus 10 will now be described. The apparatus 10 may be initially calibrated as by use of a spring gauge which is attached at opposite ends thereof to a first line which is attached to a central portion of the first clamping means 14 and a second line which is attached to a central portion of the second clamping means 22. Thereafter, pressure to line 102 is gradually incrementally increased from zero to a predetermined maximum value and the corresponding force registered by the scale attached to the web restraining means 14 and 22 is recorded for each incremental pressure value read from meter 100. A calibration graph is then constructed which enables an operator to readily determine the amount of longitudinal tension force which is being applied to a length of web material being tested from the reading of air pressure meter 100. If the same incremental force values are to be used in each web testing operation, these force values and the corresponding pressure values may be provided on a chart mounted directly on the control valve 96 to enable an operator to make the appropriate incremental force settings without referring back to other calibration information.

A small spool 56 of web material to be tested is rotatably mounted on support assembly 58. Next, an end portion of the web is pulled across the table top under raised transverse member 66 and over convex surface 44, over roll 52 and down past the second web restraining means 22.

Next, the first web restraining means is engaged with the web through movement of the plate member 66 to the clamping position illustrated in solid lines in FIG. 1. Next, the second web restraining means 22, which is positioned at a relatively elevated position due to the lack of air pressure to the cylinder units 104, 106, is clampingly engaged with the web. Next, the air compressor 90 is switched on and the control valve wheel 98, which is initially positioned at zero pressure, is turned slightly to provide a nominal pressure, e.g. 0.5 psig, which is sufficient to pull the web taught. Next, measuring means 26 is used to measure the width of the web at the mid-portion thereof located at transverse line 48. Next, the air pressure provided through line 102 is increased to a first value corresponding to a predetermined tension force value, e.g. 1.0 lb., by operation of wheel 98. The web width is then measured at this preset pressure. The pressure through line 102 is thereafter increased incrementally, e.g. in increments of 1.0 lb., up to a predetermined maximum pressure with web width measurements being made at reference position 48 after each incremental tension increase. The relative web width decrease which is produced at one tension setting is illustrated in phantom in FIG. 2.

Figure 4:
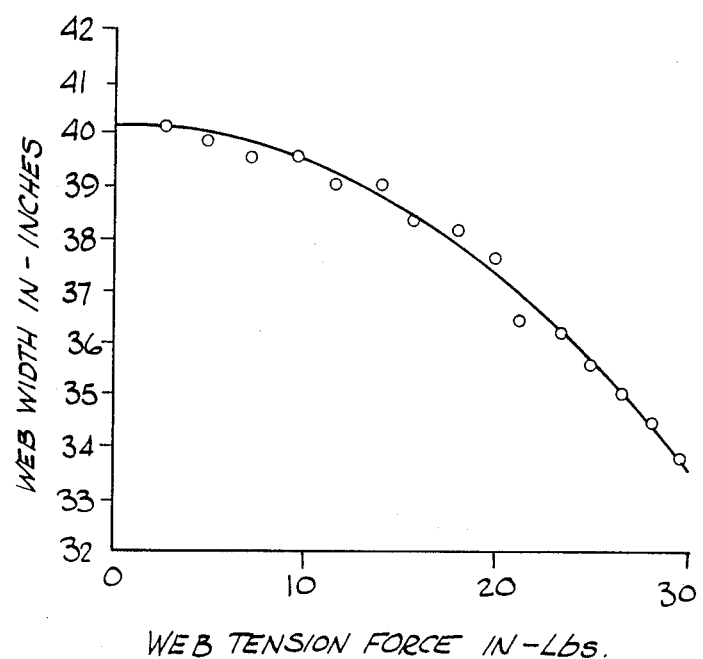
FIG. 4 is a graph of web width vs. web tension.

After all of the incremental force settings and corresponding web width measurements have been made, a graph such as illustrated in FIG. 4 is constructed, with web width comprising one coordinate of the graph and web tension comprising the other coordinate of the graph. Web width may be expressed in inches and web tension may be expressed in pounds of force. After such a graph is constructed for a particular roll of film which is to be processed, the graph is provided to operators in charge of setting up the processing machine which is to operate on the web. The operator selects the particular web width which is to be maintained by the processing machine and reads the corresponding tension value required to achieve this web width from the graph. The processing machine operator then sets the processing machine tension at the value indicated by the graph. Thus, the tested web of material is initially processed at a tension setting which is approximately correct for achieving the desired web width. Thereafter, the automated monitoring and control system of the processing machine may make minor adjustments in the web tension setting to maintain this desired web width.

It will also be appreciated that this same general procedure may be used for determining the amount of distortion in printed repeating graphics 130 on the web that may be expected under various tension settings. Graphics distortions may be predicted as being proportional to web distortion as determined in the above described manner. Alternately, the size of selected repeating graphics portions, e.g. 132, of the web may be measured directly under various stretching force conditions produced as described above. Such results may then be collected and correlated graphically. Both vertical and lateral stretching distortion may be measured and correlated with web tension.

It is contemplated that the inventive concepts herein described may be variously otherwise embodies and it is intended that the appended claims be construed to include the alternative embodiments of the invention except insofar as limited by the prior art.

What is claimed is:

1. An apparatus for determining the width variation in a length of plastic web under different longitudinal tension conditions comprising:
   (a) a generally horizontally oriented web support surface having a front edge and a rear edge and having a central longitudinal axis extending between said front and rear edges and having a transverse dimension at least as great as the unstressed transverse dimension of said web, said web support surface having a generally convex side profile having a relatively higher central portion and relatively lower end portions, said web support surface being a smooth surface having a relatively low coefficient of friction and being provided with a plurality of closely spaced, longitudinally extending lines for facilitating the initial deployment of the length of web to be tested with the longitudinal extending edges of the web positioned parallel to the central longitudinal axis of the web support surface;
   (b) a first transversely extending clamping means positioned proximate to said rear edge of said web support surface and fixedly mounted thereon for fixedly clampingly holding a portion of said length of plastic web against said web support surface, said first clamping means being adapted to provide a uniform clamping force across the entire width of said engaged portion of said web;
   (c) roll means for rollingly supporting a portion of said web hereon fixedly mounted proximate said front edge of said web support surface with the uppermost surface of said roll means positioned approximately at the same elevation as said front edge portion of said support surface;
   (d) a second, transversely extending clamping means positioned below said roll means for uniformly, clampingly engaging a portion of said web across the entire width thereof, said second clamping means being selectively longitudinally displaceable for enabling a uniform longitudinal stress to be applied to said web;
   (e) second clamping means mounting means for mounting said second clamping means in transversely fixed, longitudinally displaceable relationship with said web;
   (f) force applying means for applying a selectable amount of force against said second clamping means in a longitudinal direction whereby a selectable longitudinal tension is provided in said web; and
   (g) web width measuring means for measuring the width of said length of web at a selected portion thereof.

2. A method for determining the approximate web tension setting for a continuous web processing machine of the type having a web unwind roll, a web draw roll and a processing station positioned between the unwind roll and draw roll which performs repetitive operations on the web wherein a web to be processed is a plastic web of the type which is subject to substantial stretching and shrinking in response to relatively small tension variations in the web and wherein the processing machine is of the type which requires a preset constant web width for proper web processing, comprising:
   (a) providing a length of web material from a web roll that is to be processed;
   (b) restraining the length of web material against longitudinal movement at one end thereof;
   (c) engaging an end of the web with a longitudinally movable clamping device;
   (d) applying a selected constant test force to the movable clamping device in a longitudinal direction so as to place the web under a constant, uniform tension;
   (e) measuring the width of the web after application of the test force thereto in a predetermined longitudinal region of the web; and
   (f) recording the test force value and the measured web width associated therewith.

3. The method of claim 2 comprising the further steps of:
   (g) repeating steps (d), (e), and (f) for a plurality of different magnitude test forces;
   (h) based upon the plurality of recorded test force values and associated web widths, determining a force value corresponding to the preset constant web width for which the operating machine is desired; and
   (i) initially setting the web tension of the operating machine to a value corresponding to said determined force value.

* * * * *